United States Patent [19]

Braginetz et al.

[11] Patent Number: 4,883,471
[45] Date of Patent: Nov. 28, 1989

[54] DISPOSABLE SHIELDED MEDICAL SYRINGE

[76] Inventors: Paul A. Braginetz, 214 Oak Ridge Cir.; Mark R. Leadbetter, 1926 Spring Hill Rd.; Joseph A. Peduto, Rte. 5, all of, Staunton, Va. 24401

[21] Appl. No.: 232,775

[22] Filed: Aug. 16, 1988

[51] Int. Cl.[4] .............................................. A61M 5/32
[52] U.S. Cl. .................................... 604/195; 604/218; 604/220
[58] Field of Search ............... 604/196, 195, 187, 220, 604/218, 194, 193

[56] References Cited

U.S. PATENT DOCUMENTS 2,752,920 7/1956 Kurkjian ............................. 604/220
2,830,586 4/1958 Dann et al. ......................... 604/220
4,507,117 3/1985 Vining et al. ....................... 604/196

FOREIGN PATENT DOCUMENTS 1287742 1/1969 Fed. Rep. of Germany ...... 604/220

Primary Examiner—John D. Yasko
Attorney, Agent, or Firm—Brady, O'Boyle & Gates

[57] ABSTRACT

A disposable shielded medical syringe wherein the contaminated needle is drawn into the syringe barrel and a cap or scabbard is insertable into the open end of the syringe barrel to completely enclose the contaminated needle. A spring clip is mounted on the proximate end portion of the syringe barrel providing a stop member to prevent the syringe plunger from being pulled completely out of the barrel.

11 Claims, 3 Drawing Sheets

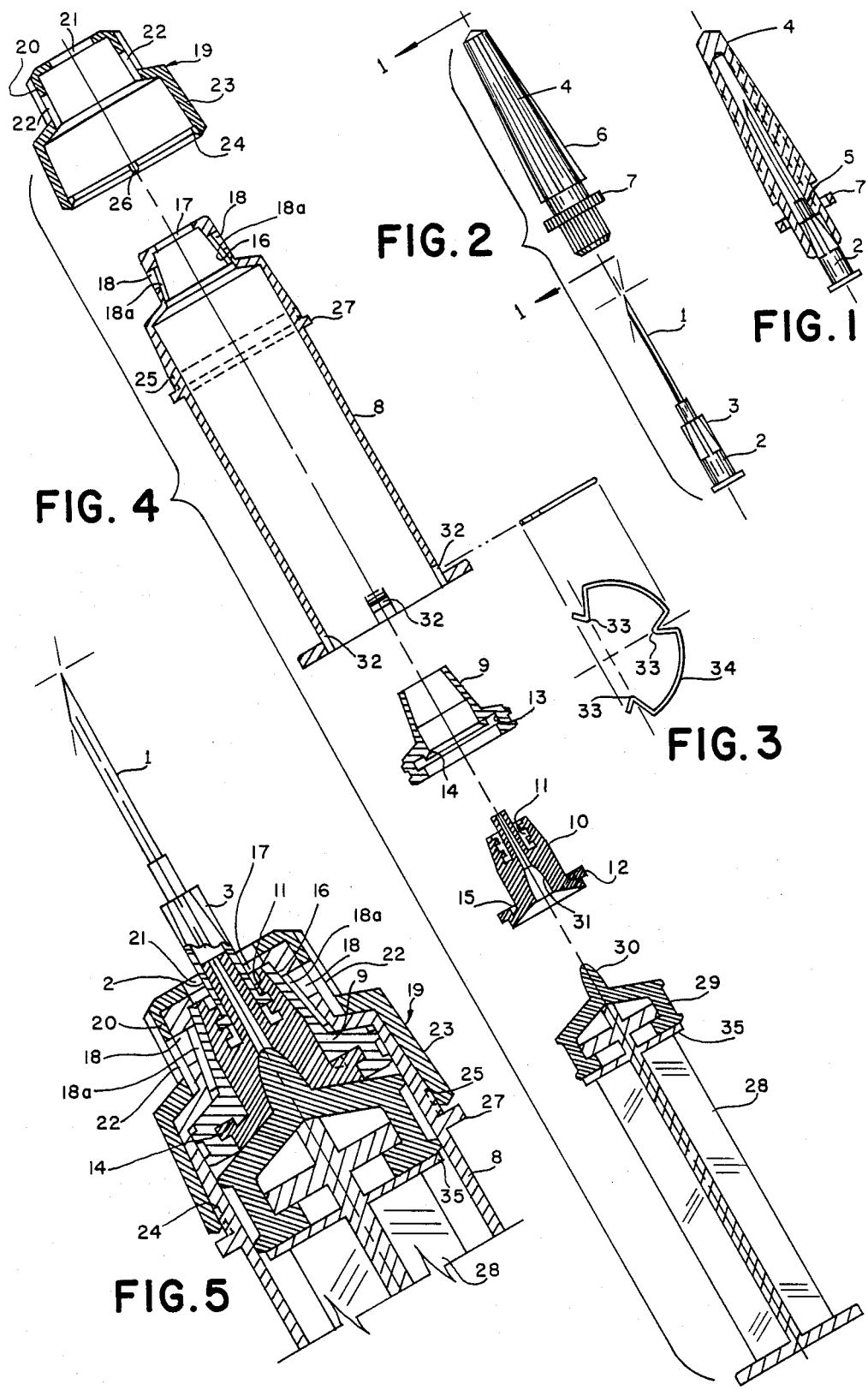

DISPOSABLE SHIELDED MEDICAL SYRINGE

BACKGROUND OF THE INVENTION

Medical personnel have to exercise the utmost of care when using conventional syringes so as not to be accidentally punctured by a contaminated syringe needle resulting in possible exposure to infectious diseases, such as acquired immune deficiency syndrome (AIDS) or serum hepatitis when injecting a medicament into a patient.

While various safeguards have been provided, such as protective caps for covering a used needle and sharps containers for the disposal of the used needle, it has been found that the chance of accidental puncture is most likely to occur during the manipulation of the syringe to either cap the needle or inverting the used needle into the sharps container.

In an effort to improve the safeguards for used syringe needles, it has been proposed to provide the syringe with a sleeve slidably mounted on the syringe barrel and movable from a retracted position on the syringe barrel to an extended position at the distal end of the barrel, to thereby provide a shield surrounding the used needle. The sleeve is releasably held in the retracted and extended positions by detents which are manually actuated by the user. These sleeve-type shields have not proven entirely satisfactory due, mainly, to the manual dexterity required by the user to release one detent for sliding the sleeve to the needle protecting position and then to actuate another detent for holding the sleeve in the extended position.

In order to overcome the disadvantages experienced in hitherto employed shielded medical syringes, the disposable shielded medical syringe of the present invention has been devised which comprises, essentially, a syringe barrel including a plunger having a piston on the end thereof slidably mounted in the barrel. The syringe needle is connected to a second piston slidably mounted within the barrel and located between the distal end of the barrel and the plunger piston. By this construction and arrangement, medicament is dispensed from the syringe by pushing the plunger toward the distal end of the barrel, and the needle and associated piston are drawn inwardly into the barrel when the plunger is pulled back toward the proximate end of the barrel, whereby the used needle is shielded by the syringe barrel. To complete the shielding of the used needle, a cap or scabbard is inserted into the distal end of the syringe barrel. Vent holes and an associated closure are provided on the distal end portion of the syringe barrel, whereby the vent holes are closed during the dispensing of the medicament from the syringe and opened during the retraction of the syringe plunger to thereby facilitate the drawing of the used needle and associated piston to the shielded position within the syringe barrel.

A spring clip is mounted on the proximate end portion of the syringe barrel providing a stop member to prevent the syringe plunger from being pulled completely out of the barrel.

The medical syringe of the present invention thus provides a disposable shielded syringe needle requiring minimal manipulation to move the used needle to the shielded position thereby providing an improved safeguard for medical personnel against exposure to infectious diseases.

BRIEF DESCRIPTION OF THE DRAWINGS

FIG. 1 is an elevational view of a conventional syringe needle showing a cap or scabbard in section mounted on the needle;

FIG. 2 is an exploded view of the needle and cap assembly shown in FIG. 1;

FIG. 3 is a plan view of a spring clip employed as a stop member in the syringe barrel to prevent complete withdrawal of the syringe plunger from the barrel;

FIG. 4 is a exploded view of the syringe of the present invention without the needle and cap assembly illustrated in FIGS. 1 and 2;

FIG. 5 is a enlarged fragmentary, sectional view of the syringe taken along line 5—5 of FIG. 7;

DESCRIPTION OF THE PREFERRED EMBODIMENTS

Figure 6:
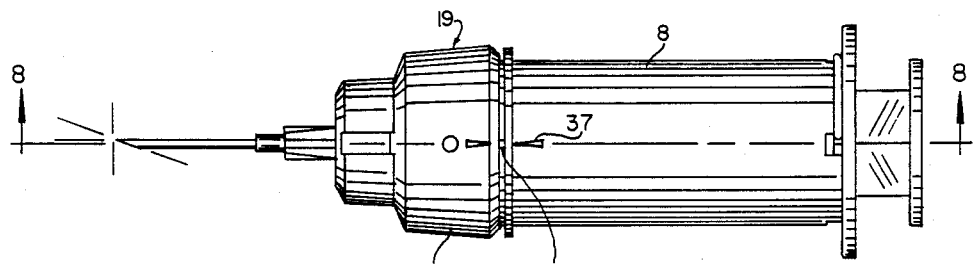
FIG. 6 is a top plan view of the syringe showing the vent hole closure at a position closing the vents when dispensing the medicament from the syringe.

Referring to the drawings and more particularly to FIGS. 1 and 2, a conventional syringe needle 1 is shown having a Luer Lock hub portion 2 having lands 3. The needle is provided with a cap or cover 4 slidably mounted on the hub portion 2 of the needle, the lands 3 of the needle hub being engageable with a rib 5 integral with the interior wall of the cap 4. The exterior wall of the cap 4 is provided with integral, resilient lands 6 and a flange portion 7.

FIGS. 4 and 5 illustrate the components of the syringe assembly of the present invention to which the syringe needle 1 and associated cap 4 of FIGS. 1 and 2 are adapted to be connected. The syringe assembly comprises a cylinder or barrel 8 having a hollow piston 9 slidably mounted therein. The piston 9 carries a Luer Lock member 10 into which the needle hub portion 2 is threadably secured as at 11. The member 10 is provided with an annular flange 12 which is received within a similarly configured groove 13 provided in the end portion of the piston 9, to thereby sealably secure the Luer Lock member 10 within the piston 9. To prevent rotation of the Luer Lock member 10 relative to the piston 9 during the connection of the needle 1 thereto, the piston 9 is provided with an axially extending tab 14 extending into a recess 15 provided in the oppositely extending face of the Luer Lock member 10. The piston 9 tapers inwardly and conforms to a conical portion 16 on the distal end of the cylinder 8, which end also is provided with a longitudinally extending aperture 17 through which the needle 1 extends. The distal end portion of the cylinder 8 is also provided with transversely extending apertures or ports 18 and longitudinally extending channels 18a through which the interior of the cylinder communicates with the atmosphere.

In order to selectively open and close the cylinder apertures 18, a closure 19 is provided having a nose portion 20 configured to receive the tapered end portion of the barrel 8 and having an aperture 21 on the end wall thereof through which the needle hub 3 extends. The side wall of the nose portion 20 is provided with a pair of apertures 22 alignable with the apertures 18 in the distal end portion of the cylinder 8. The closure 19 also includes a skirt portion 23 which extends around the distal end portion of the cylinder 8, the lower edge portion of the skirt 23 having an inwardly turned flange or bead 24 snappingly engageable underneath an annular rib 25 provided on the outer wall of the cylinder 8, whereby the closure 19 is rotatably mounted on the distal end portion of the cylinder 8, to selectively open and close the cylinder apertures 18. In order that the closure 19 can be releasably held at the selected open or closed positions, the lower end portion of the skirt 19 is provided with a plurality of radially extending notches 26 adapted to receive corresponding detent ribs 26a (FIGS. 6 and 7) on the outer wall of the cylinder in proximity to an annular flange 27 on the outer wall of the cylinder 8 providing a finger piece when using the syringe.

To complete the structure of the syringe assembly of the present invention, a plunger 28 having a piston 29 is slidably mounted within the proximate end portion of the cylinder 8, the piston 29 having a projection 30 receivable within a similarly configured aperture 31 in the Luer Lock member 10. As will be seen in FIG. 13, the proximate end portion of the cylinder wall is provided with a plurality of apertures 32 for receiving inwardly extending finger portions 33 of a spring clip 34 mounted on the exterior surface of the cylinder wall. By this construction and arrangement, the spring clip fingers 33 are adapted to engage the plunger flange 35 adjacent the piston 29, to thereby prevent complete withdrawal of the plunger 28 from the cylinder 8.

Figures 8, 9, 10:
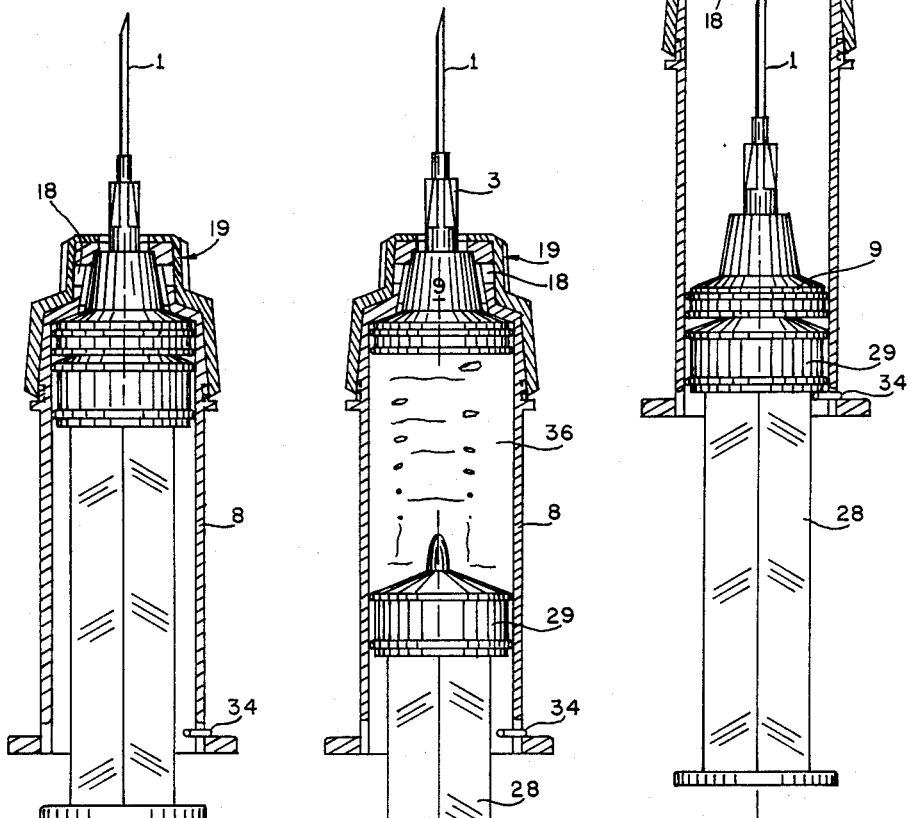
FIG. 8 is a view taken along line 8—8 of FIG. 6.
FIG. 9 is a sectional view of the syringe illustrating the relative positions of the plunger piston, needle piston and vent closure when dispensing a medicament from the syringe.
FIG. 10 is a sectional view of the syringe illustrating the relative positions of the plunger piston, needle piston and vent closure when the used needle has been drawn to the shielded position within the syringe barrel.
Figure 11:
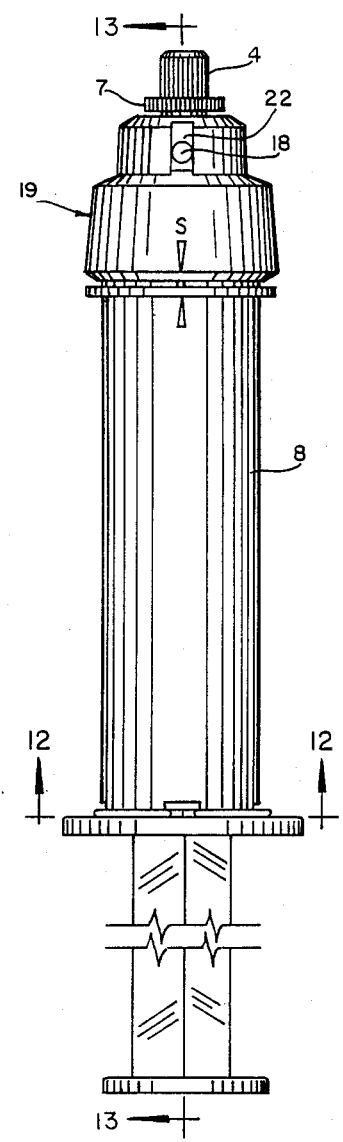
FIG. 11 is a top plan view of the syringe in the retracted position as shown in FIG. 10, with the needle cap inserted into the opening in the distal end portion of the barrel.
Figure 12:
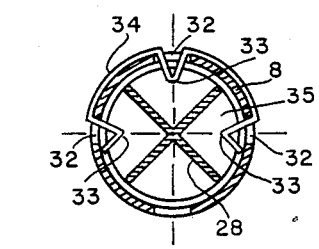
FIG. 12 is a view taken along line 12—12 of FIG. 11.

In the operation of the disposable shielded medical syringe of the present invention thus far described, as will be seen in FIG. 9, the syringe barrel 8 is provided with a medicament 36 and the closure 19 is at a position to close the ports 18. To dispense the medicament through the needle, the plunger 28 and associated piston 29 is pushed inwardly to the position shown in FIG. 8. After the medicament has been dispensed, the closure 19 is rotated to align the closure apertures 22 with the cylinder ports 18 as shown in FIG. 5 to thereby communicate the ports with the atmosphere. The plunger 28 is then pulled outwardly toward the proximate end of the barrel 8 to create a vacuum within the barrel between the pistons 9 and 29. The piston 9 is thus subjected to a differential pressure; namely, the reduced pressure or vacuum on the face of the piston within the cylinder and atmospheric pressure on the end of the piston 9 facing the ports 18 and 22, thereby causing the piston 9 and associated contaminated needle 1 to be drawn inwardly of the cylinder 8 to the shielded position as shown in FIG. 10.

Figure 13:
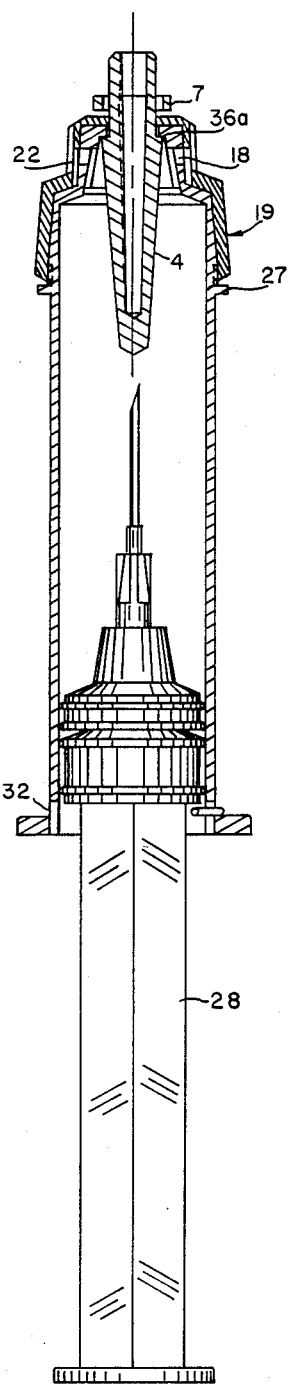
FIG. 13 is a view taken along line 13-13 of FIG. 11.
Figure 14:
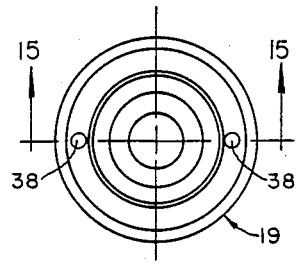
FIG. 14 is an end view of another embodiment of a vent closure.
Figure 15:
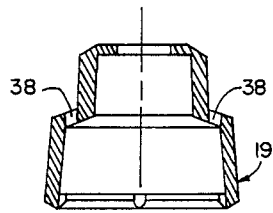
FIG. 15 is a view taken along line 15—15 of FIG. 14.
Figure 16:
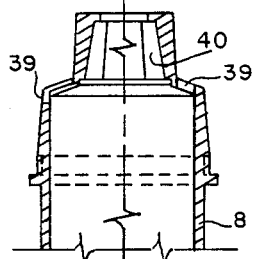
FIG. 16 is a fragmentary sectional view illustrating other embodiments of the distal end portion of the syringe barrel for use with the closure shown in FIGS. 14 and 15.

As will be seen in FIG. 13, the contaminated needle is completely enclosed by inserting the cap 4 in an upside-down manner through the closure aperture 21, and cylinder opening 17. The cap flange portion 7 prevents the cap from being inserted completely into the barrel 4, and the ends of the cap lands 6 engage the portion of the end wall of the distal end of the barrel surrounding the aperture 17 as at 36a to prevent pulling of the cap 4 out of the barrel. The cap 4 will thus prevent the contaminated needle 1 from being extended outwardly through the barrel 8 after use.

Figure 7:
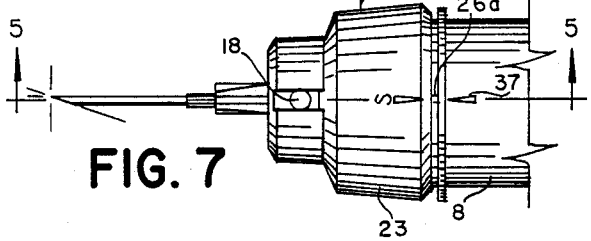
FIG. 7 is a fragmentary top plan view of the syringe showing the position of the vent hole closure at a position opening the vents.

Referring to FIGS. 6 and 7, suitable indicia are provided on the closure 19 and barrel 8 to facilitate the use of the disposable shielded medical syringe, wherein an arrow 37 is provided on the barrel 8 alignable with a selected arrow "0" or "S" on the closure skirt portion 23. In FIG. 6, the closure 19 has been rotated to the operational position wherein the barrel ports 18 are closed to the atmosphere, and in FIG. 7 the closure has been rotated to the safety position wherein the ports 18 are open to the atmosphere.

While the cylinder ports 18 and closure apertures 22 have been shown and described as being transverse in connection with the embodiment of the invention illustrated in FIGS. 3 to 13, FIGS. 14 and 15 illustrate another embodiment wherein the closure 19 is provided with longitudinally extending apertures 38 alignable with longitudinally extending ports 39 on the distal end portion of the cylinder 8, which is also provided with a polygonal inner wall surface 40.

Figure 17:
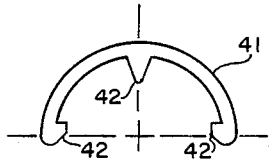
FIG. 17 is a plan view of another embodiment of a spring stop member for the proximate end of the barrel.

FIG. 17 illustrates another embodiment of spring stop to prevent complete removal of the plunger from the barrel wherein a flat spring 41 is provided with a plurality of fingers 42 insertable through the apertures 32 in the barrel wall.

Figure 18:
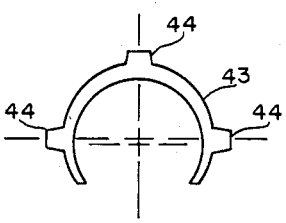
FIG. 18 is a plan view of yet another embodiment of a spring stop member for the proximate end of the barrel.

FIG. 18 illustrates ye another embodiment of the stop spring wherein an internal spring clip 43 is provided with fingers 44 which would extend outwardly from the barrel apertures 32.

From the above description, it will be readily apparent to those skilled in the art that the disposable shielded medical syringe of the present invention provides an improved disposable shielded syringe needle requiring minimal manipulation to move the contaminated needle to the shielded position to thereby provide an improved safeguard for medical personnel against exposure to infectious diseases.

It is to be understood that the forms of the invention herewith shown and described are to be taken as preferred examples of the same, and that various changes in the shape, size and arrangement of parts may be resorted to, without departing from the spirit of the invention or scope of the subjoined claims.

We claim:

1. A disposable shielded medical syringe comprising a syringe barrel, a plunger slidably mounted in said barrel, a piston secured to the distal end of the plunger and being in sealing, sliding engagement with the inner wall of the barrel, a second piston slidably mounted in said barrel and being in sealing, sliding engagement with the inner wall of the barrel and being positioned between the distal end portion of the barrel and the plunger piston, a syringe needle extending outwardly longitudinally of the barrel at the distal end thereof, means for connecting the syringe needle to said second piston, vent means communicating the interior distal end portion of the barrel with the atmosphere, closure means for closing the communication of the interior distal end portion of the barrel with the atmosphere, and a medicament contained within the barrel between the plunger piston and the second piston, whereby when the vent means are closed the medicament is dispensed through the needle by pushing the plunger inwardly of the barrel, and when the vent means are open the second piston and associated contaminated needle is drawn inwardly to a shielded position within the barrel by pulling the plunger in a direction toward the proximate end of the barrel.

2. A disposable shielded medical syringe according to claim 1, wherein the means for connecting the syringe needle to the second piston comprises, a Luer Lock member operatively connected to said second piston, said needle having a Luer Lock hub portion, said needle Luer Lock hub portion being threadably connected to said Luer Lock member.

3. A disposable shielded medical syringe according to claim 1, wherein said vent means comprises a plurality of ports in the distal end portion of said barrel, and a plurality of apertures in the closure means alignable with said ports.

4. A disposable shielded medical syringe according to claim 3, wherein the closure means comprises a nose portion configured to receive the distal end portion of the barrel, and a skirt portion extending around the distal end portion of the barrel.

5. A disposable shielded medical syringe according to claim 4, wherein a bead is provided on the lower edge of said skirt portion, and an annular rib provided on the outer wall of the barrel, said bead being snappingly engageable underneath said rib, whereby the closure is rotatably mounted on the distal end portion of the barrel to selectively open and close the barrel ports.

6. A disposable shielded medical syringe according to claim 5, wherein detent means are provided between the closure skirt and barrel to releasably hold the closure in the selected open and closed positions.

7. A disposable shielded medical syringe according to claim 6, wherein indicia means are provided on the closure skirt and barrel to indicate the open and closed positions.

8. A disposable shielded medical syringe of the type wherein the syringe needle is retracted into the syringe barrel through the open end of the barrel, the improvement comprising, a needle cap insertable into the open end of the barrel to prevent the contaminated needle from being moved from the retracted, shielded position outwardly through the open end of the barrel.

9. A disposable shielded medical syringe according to claim 8, wherein the needle cap includes a plurality of integral, resilient lands on the outer wall thereof, and a flange portion positioned between the ends of the lands and the open end of the cap, said cap being inserted into the open end of said barrel in an upside-down manner, whereby the flange portion prevents the cap from being inserted completely into the barrel and the ends of the cap lands engage the distal end portion of the barrel surrounding the open end of said barrel to prevent pulling of the cap out of the barrel.

10. A disposable shielded medical syringe according to claim 1, wherein spring stop means is mounted on the proximate end portion of the barrel adapted to be engaged by the syringe piston when fully retracted, to thereby prevent complete removal of the syringe piston from the barrel.

11. A disposable shielded medical syringe according to claim 8, wherein spring stop means is mounted on the proximate end portion of the barrel adapted to be engaged by the syringe piston when fully retracted, to thereby prevent complete removal of the syringe piston from the barrel.

* * * * *